United States Patent

Brindell et al.

[11] 4,038,327
[45] July 26, 1977

[54] 3,5-DISUBSTITUTED-4-HYDROXYBENZYL DERIVATIVE

[75] Inventors: Gordon D. Brindell, Crystal Lake; Rudy F. Macander, Cary, both of Ill.

[73] Assignee: The Quaker Oats Company, Chicago, Ill.

[21] Appl. No.: 257,178

[22] Filed: May 26, 1972

[51] Int. Cl.$^2$ ............................................. C07C 37/00
[52] U.S. Cl. ............................... 260/619 R; 260/570.9; 260/611 A; 260/624 R; 260/570 R
[58] Field of Search ................. 260/570.9, 625, 619 R, 260/624 R

[56] References Cited

U.S. PATENT DOCUMENTS

| | | | |
|---|---|---|---|
| 3,006,969 | 10/1961 | Koetitz | 260/624 |
| 3,052,728 | 9/1962 | Rocklin | 260/619 |
| 3,081,335 | 3/1963 | Morris et al. | 260/624 X |
| 3,091,645 | 5/1963 | Rocklin | 260/619 |
| 3,496,211 | 2/1970 | Dexter et al. | 260/465 |

*Primary Examiner*—Robert V. Hines
*Attorney, Agent, or Firm*—Joseph P. O'Halloran; Grace J. Fishel

[57] ABSTRACT

A new series of compounds having the following formula is disclosed:

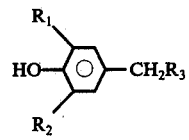

wherein $R_1$ and $R_2$ are independently aralkyl or alkyl with the proviso that the aralkyl group contains no branching on the carbon alpha to the phenylene group and the alkyl group contains no branching on the carbon alpha to the phenylene group but has at least one branch on the carbon beta to the phenylene group; $R_3$ is hydroxy, —$OR_4$ or

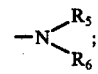

$R_4$, $R_5$, and $R_6$ are alkyl, cycloalkyl, aralkyl, aryl, or alkaryl and $R_6$ may additionally be hydrogen; said compounds are useful as antioxidants for polyolefins.

1 Claim, No Drawings

3,5-DISUBSTITUTED-4-HYDROXYBENZYL DERIVATIVE

BACKGROUND OF THE INVENTION

1. Field of the Invention

This invention relates to a new class of 3,5-disubstituted-4-hydroxybenzyl derivatives useful for stabilizing polyolefins.

2. Description of the Prior Art

In U.S. Pat. Nos. 2,962,531, 3,043,774 and 3,208,859, T. H. Coffield described compounds of the general formula:

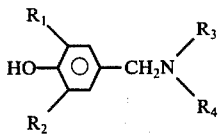

(Formula I)

wherein $R_1$ is an alkyl group containing from 1 to 12 carbon atoms, $R_2$ is an alkyl group containing from 3 to 12 carbon atoms which is branched on the alpha carbon atom, $R_3$ is selected from the group consisting of alkyl, cycloalkyl, aralkyl, aryl, and alkaryl and

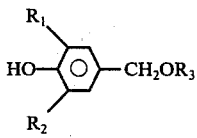

and $R_4$ is selected from the group consisting of hydrogen, alkyl, cycloalkyl, aralkyl, aryl, and alkaryl. These compounds are useful as antioxidants for organic materials.

In U.S. Pat. Nos. 2,838,571 and 2,954,345, A. H. Filbey described compounds of the general formula:

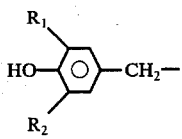

(Formula II)

wherein $R_1$ is an alkyl group containing from 3 to 8 carbon atoms and is branched on the alpha carbon atom, $R_2$ is an alkyl group containing from 1 to 8 carbon atoms, and $R_3$ is selected from the group consisting of alkyl, cycloalkyl, aralkyl and alkenyl. These compounds are useful as antioxidants for organic materials.

SUMMARY OF THE INVENTION

The present invention differs from the prior art in the following ways:

1. A new class of 3,5-disubstituted-4-hydroxybenzyl derivatives is described wherein the substituents in the 3,5-position are not branched on the alpha carbon atom but has at least one branch on the beta carbon.

2. The new class of 3,5-disubstituted-4-hydroxybenzyl derivatives are unexpectedly good antioxidants for polyolefins compared to those derivatives wherein the substituents in the 3,5-position are branched on the alpha carbon atom.

The invention may be briefly described as a composition having the formula:

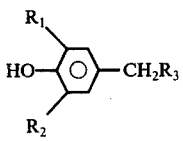

(Formula III)

wherein $R_1$ and $R_2$ are independently aralkyl or alkyl with the proviso that the aralkyl group contains no branching on the carbon alpha to the phenylene group or the alkyl group contains no branching on the carbon alpha to the phenylene group but has at least one branch on the carbon beta to the phenylene group; $R_3$ is hydroxy, $-OR_4$ or

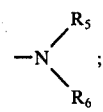

$R_4$, $R_5$, and $R_6$ are alkyl, cycloalkyl, aralkyl, aryl or alkaryl and $R_6$ may additionally be hydrogen.

Where $R_1$ or $R_2$ are alkyl in Formula III, we mean a primary alkyl group wherein there is at least one alkyl branch on the carbon in said primary alkyl group beta to the phenylene group to which it is attached. We prefer that when $R_1$ or $R_2$ is alkyl that the alkyl group contains from 4 to 10 carbon atoms.

When $R_1$ or $R_2$ in Formula III are aralkyl we are to be understood to mean a group of the following structure:

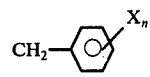

(Formula IV)

wherein X is alkyl, alkoxy or halogen, and $n$ is an integer between 0 and 5 inclusive. We prefer that the aralkyl group contains less than 20 carbon atoms. Where the aralkyl group is substituted with halogen, the halogen group may be chloro, bromo, iodo, or fluoro, for example. Where the aralkyl group is substituted with alkyl or alkoxy groups, these groups preferably contain from 1 to 12 carbon atoms which may be straight or branched chain. Suitable aralkyl groups include the following as long as the above-mentioned proviso is satisfied: benzyl, ar-chlorobenzyl, ar-bromobenzyl, ar-iodobenzyl, ar-fluorobenzyl, ar-methoxybensyl, ar-ethoxybenzyl, ar-methylbenzyl, ar-ethylbenzyl, or ar-tert-butylbenzyl.

In the compound of Formula III, it is preferable that the hydrocarbon radicals of the groups designated above as $R_3$ and $R_4$ contain the following ranges of carbon atoms: Alkyl, 1 to 12; cycloalkyl, 5 to 6; aralkyl, 7 to 11; aryl, 6 to 10; and alkaryl, 7 to 15. The alkyl, cycloalkyl, aralkyl, and alkaryl groups may be straight or branched chain. It is particularly preferred that both $R_1$ and $R_2$ be aralkyl groups wherein there is no alkyl branching on the carbon alpha to the phenylene group.

Examples of specific 3,4-disubstituted-4-hydroxybenzyl derivatives within the scope of Formula III and useful in the practice of this invention are the following:

N,N-dimethyl-3-methyl-5-isobutyl-4-hydroxybenzylamine;

N,N-dimethyl-3 -ethyl-5(2'-methylbutyl)-4-hydroxybenzylamine;

N,N-dimethyl-3-isopropyl-5(2'-methylpentyl)-4-hydroxybenzylamine;
N,N-dimethyl-3-tert-butyl-5(2'-ethylhexyl)-4-hydroxybenzylamine;
N,N-diethyl-3-ethyl-5(2'-methylbutyl)-4-hydroxybenzylamine;
N-cyclohexyl-3-isopropyl-5(2'-methylpentyl)-4-hydroxybenzylamine;
N-benzyl-3-tert-butyl-5(2'-ethylhexyl)-4-hydroxybenzylamine;
N-phenyl-3-methyl-5-isobutyl-4-hydroxybenzylamine;
N-3,5-xylyl-3-ethyl-5(2'-methylbutyl)-4-hydroxybenzylamine;
N-p-butylbenzyl-3-isopropyl-5(2'-methylpentyl)-4-hydroxybenzylamine;
N-α-naphthyl-3-tert-butyl-5(2'-ethylhexyl)-4-hydroxybenzylamine;
N-p-tolyl-3-ethyl-5(2'-methylbutyl)-4-hydroxybenzylamine;
3,5-diisobutyl-4-hydroxybenzyl alcohol
3,5-di(2'-methylbutyl)-4-hydroxybenzyl alcohol
3,5-di(2'-ethylbutyl)-4-hydroxybenzyl alcohol
3,5-di(2'-ethylhexyl)-4-hydroxybenzyl alcohol
3,5-dibenzyl-4-hydroxybenzyl alcohol
3,5-di-o-chlorobenzyl-4-hydroxybenzyl alcohol
3,5-di-p-chlorobenzyl-4-hydroxybenzyl alcohol
3,5-di-p-methylbenzyl-4-hydroxybenzyl alcohol
3,5-di-p-methoxybenzyl-4-hydroxybenzyl alcohol
3,5-diisobutyl-4-hydroxybenzyl ethyl ether
3,5-di(2'-methylbutyl)-4-hydroxybenzyl ethyl ether
3,5-di(2'-ethylbutyl)-4-hydroxybenzyl ethyl ether
3,5-dibenzyl-4-hydroxybenzyl methyl ether
3,5-di-o-chlorobenzyl-4-hydroxybenzyl methyl ether
3,5-di-p-chlorobenzyl-4-hydroxybenzyl methyl ether
3,5-di-p-ethylbenzyl-4-hydroxybenzyl isopropyl ether
3,5-di-p-ethoxybenzyl-4-hydroxybenzyl ethyl ether The 3,5-disubstituted-4-hydroxybenzyl alcohols of Formula III are prepared by contacting (1) a 2,6-disubstituted phenol in which the substituents conform with the group designated $R_1$ and $R_2$, (2) formaldehyde, and (3) a sterically hindered monohydric alcohol such as isopropyl alcohol in the presence of a catalytic quantity of a metallic hydroxide condensation catalyst, said metallic hydroxide being a metal selected from the group consisting of alkali and alkaline earth metals.

The 3,5-disubstituted-4-hydroxybenzyl ethers of Formula III are prepared by contacting (1) a 2,6-disubstituted phenol in which the substituents conform with the groups designated $R_1$ and $R_2$, (2) formaldehyde, and (3) a monohydric alcohol which conforms with the requirements of the group $-OR_4$ designated above, in the presence of a catalytic quantity of a metallic hydroxide condensation catalyst, said metallic hydroxide being a metal selected from the group consisting of alkali and alkaline earth metals. Suitable preparations are described in U.S. Pat. No. 2,838,571 and in the following examples.

The 3,5-disubstituted-4-hydroxy-benzylamines of Formula III are prepared by contacting (1) a 2,6-disubstituted phenol in which the substituents conform with the groups designated $R_1$ and $R_2$, (2) formaldehyde, and (3) a primary or secondary amine which conforms with the requirements of the group

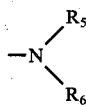

designated above. In conducting this process a monohydric alcohol containing from 1 to 6 carbon atoms is preferably used as the reaction solvent. A typical preparation is set forth by way of example below. Other suitable preparations are described in U.S. Pat. No. 2,962,531.

The term "polyolefin" as used herein means those polymers derived from monoolefins having a terminal double bond. Examples of such alpha polyolefins include but are not limited to the following: polyethylene, polypropylene, poly-4-methylpentene-1, poly-1-butene, poly-3-methylbutene-1, and copolymers thereof.

In general, the 3,5-disubstituted-4-hydroxybenzyl derivatives of Formula III should be used with the polyolefin to be stabilized in an amount effective and sufficient to stabilize the material. The requisite amount will, of course, depend both on the efficiency of the particular 3,5-disubstituted-4-hydroxybenzyl derivative, and on the nature of the polyolefin in which it is employed. It has been our experience that from 0.01 to 10 percent by weight based on the weight of the polyolefin is sufficient. Amounts down to as little as 0.0001 percent by weight may be effective in some cases.

It is to be understood that the stabilizing effect of the 3,5-disubstituted-4-hydroxybenzyl derivatives of Formula III is considerably enhanced by conventional synergists such as certain sulfides and polysulfides. The synergist is used in conventional amounts. For example an amount of synergist from about 0.1 to about 1 percent by weight of the polyolefin to be stabilized is satisfactory but we prefer to use from 0.1 to 0.5 percent by weight.

As sulfides there may be mentioned dialkylsulfides, particularly wherein the alkyl groups are long chain such as dodecyl groups since the lower dialkylsulfides are too volatile to be effective, di(substituted)alkylsulfides particularly esters of bis-arboxyalkyl sulfides such as dilauryl, distearyl, ditridecyl, or dioctadecyl thiodipropionates or thiodibutyrates, dibenzylsulfides such as bis-(2-hydroxy-5-methylbenzyl)sulfide and bis(3-tert-butyl-2-hydroxy-5-methoxybenzyl)sulfide, diaryl sulfide, sulfides such as diphenyl sulfide, dicresyl sulfide, 2,2'-di-hydroxy-5,5'-dimethyl diphenyl, diphenyldisulfide, dialkyldithiophosphates such as bis(diisopropyldithiophosphoryl)disulfide, and dialkyldithiophosphatomethylphenols.

It will further be understood that the polyolefin in addition to containing a stabilizing amount of 3,5-disubstituted-4-hydroxybenzyl derivative of Formula III and a synergist may contain such other ingredients as other antioxidants, coloring agents, fillers, curing agents, etc.

DESCRIPTION OF THE PREFERRED EMBODIMENTS

The following embodiments of this invention are shown for the purpose of illustrating the invention and demonstrate the best mode for practicing the invention. It will be apparent to those skilled in the art that various changes and modifications may be made therein without departing from the spirit and scope of the invention as it is more precisely defined in the subjoined claims.

EXAMPLE 2

In a 1000-ml, 3-neck flask equipped with a condenser, thermometer, and dropping funnel 42 g of 2,6-diisobutylphenol, 200 ml of ethanol and 62 g of dimethylamine was placed and cooled to 80° C. Through the dropping funnel 30 g of a formaldehyde solution (37 percent by weight of formaldehyde in water) was added to the flask over a period of 15 minutes. The contents of the flask was maintained at reflux for 7 hours.

The ethanol was stripped from the reaction mixture, then the product was dissolved in benzene and extracted with water. The benzene phase was dried with magnesium sulfate and then the benzene stripped from the product to yield an oily residue which was crude N,N-dimethyl-3,5-diisobutyl-4-hydroxybenzylamine.

The product was dissolved in 800 ml of n-hexane and contacted with sufficient hydrochloric acid to form the amine salt. The n-hexane was decanted. The salt dissolved in methylene dichloride, and then extracted with a solution of 8 g of sodium hydroxide in water. The product which was in the methylene dichloride layer was dried with magnesium sulfate. The methylene dichloride was vacuum distilled from the purified product.

EXAMPLE 2

Following the procedure of Example 1 except that 2,6-di(2'-ethylhexyl)phenol was substituted for the 2,6-diisobutylphenol N,N-dimethyl-3,5-di(2'-ethylhexyl)-4-hydroxybenzylamine was prepared.

EXAMPLE 3

In the reaction equipment of Example 1, 10.3 g of 3,5-diisobutylphenol, 2.1 g of a formaldehyde solution (37 percent by weight of formaldehyde in water), 20.0 ml of isopropyl alcohol, and 0.3 g of potassium hydroxide were placed and the contents of the flask maintained at a temperature between 35°–40° C. for 3 hours while being stirred continuously.

The product was dissolved in n-hexane and extracted with water. The water phase was separated leaving the n-hexane phase containing the product. The n-hexane phase was cooled and the product separated by filtration. The crystalline product was further washed with cold n-hexane. The purified product was 3,5-diisobutyl-4-hydroxybenzyl alcohol having a melting point of 82°–90° C.

EXAMPLE 4

The performance of several 3,5-disubstituted-4-hydroxybenzyl derivatives as an antioxidant for polypropylene was determined in the following tests:

In Test 1 an 80 g sample of Hercules Pro-Fax 6501 polypropylene powder was admixed in a Brabender Plasticorder in which the mixing chamber was heated to about 200° C. The material was mixed for 5 to 10 minutes until the polypropylene had a workable consistency. A sample of the material was then removed and molded into a 5 mil film. One inch diameter circles of the film were cut out and put into an oven maintained at 140° C. After 1 hour in the oven, the sample crumbled.

In Test 2, 0.24 g of dilaurylthiodipropionate was mixed with the 80 g of polypropylene powder and a sample tested for heat aging as in Test 1. The sample lasted for 70 hours before it crumbled.

TABLE I

| Test No. | Antioxidant | Synergist | Hours Before Crumbling |
|---|---|---|---|
| 1 | 0 | no | 1 |
| 2 | 0 | yes | 70 |
| 3 | 2,6-di-tert-butyl-4-hydroxybenzyl alcohol | no | 3 |
| 4 | 2,6-di-tert-butyl-4-hydroxybenzyl alcohol | yes | 211 |
| 5 | 2,6-diisobutyl-4-hydroxybenzyl alcohol | no | 8 |
| 6 | 2,6-diisobutyl-4-hydroxybenzyl alcohol | yes | 571 |
| 7 | N,N-dimethyl-3,5-di-tert-butyl-4-hydroxybenzylamine | no | 5 |
| 8 | N,N-dimethyl-3,5-di-tert-butyl-4-hydroxybenzylamine | yes | 268 |
| 9 | N,N-dimethyl-3,5-diisobutyl-4-hydroxybenzylamine | no | 16 |
| 10 | N,N-dimethyl-3,5-diisobutyl-4-hydroxybenzylamine | yes | 403 |
| 11 | N,N-dimethyl-3,5-di(2'-ethylhexyl)-4-hydroxybenzylamine | no | 16 |
| 12 | N,N-dimethyl-3,5-di(2'-ethylhexyl)-4-hydroxybenzylamine | yes | 595 |

The above examples clearly demonstrate the accomplishment of this invention. Examples 1–3 inclusive demonstrate our preferred method for obtaining the 3,5-disubstituted-4-hydroxybenzyl derivatives of Formula III.

In Example 4 a comparison of Test 5 with Test 3 and more particularly Test 6 with Test 4 clearly demonstrates the superiority of the 3,5-disubstituted-4-hydroxybenzyl alcohols of Formula III as antioxidants in polyolefins over the conventional antioxidant 3,5-di-tert-butyl-4-hydroxybenzyl alcohol.

A comparison of Test 9 and 11 with Test 7 and more particularly Test 10 and 12 with Test 8 clearly demonstrates the superiority of the 3,5-disubstituted-4-hydroxybenzylamines of Formula III as antioxidants in polyolefins over the known antioxidant 3,5-di-tert-butyl-4-hydroxybenzylamine. Tests 1, 2, 3, 4, 7, and 8 are not embodiments of our invention but were prepared for the purposes of comparision with the results from use with the 3,5-di-substituted-4-hydroxybenzyl derivatives of Formula III.

3,5-Di-substituted-4-hydroxybenzyl methyl ether of Formula III were compared with 3,5-di-tert-butyl-4-hydroxybenzyl methyl ether and were also found to be superior antioxidants, particularly in the presence of conventional sulfide synergists, for polypropylene.

From the foregoing description we consider it to be clear that the present invention contributes a substantial benefit to the antioxidant art by providing a new and useful antioxidant for polyolefins.

We claim:

1. The composition which is 3,5-dibenzyl-4-hydroxybenzyl alochol.

* * * * *